United States Patent [19]

Paine

[11] Patent Number: 4,967,002
[45] Date of Patent: Oct. 30, 1990

[54] PROCESSES FOR SQUARAINE COMPOUNDS

[75] Inventor: Anthony J. Paine, Mississauga, Canada

[73] Assignee: Xerox Corporation, Stamford, Conn.

[21] Appl. No.: 68,500

[22] Filed: Jul. 1, 1987

[51] Int. Cl.$^5$ ............................................. C07C 85/00
[52] U.S. Cl. .................................................... 564/307
[58] Field of Search ......................... 564/307; 430/59; 560/24, 187

[56] References Cited

U.S. PATENT DOCUMENTS

| | | | |
|---|---|---|---|
| 4,239,904 | 12/1980 | Kesling, Jr. | 560/157 |
| 4,251,667 | 2/1981 | Kesling, Jr. | 560/24 |
| 4,523,035 | 6/1985 | Yanus | 564/307 |
| 4,524,218 | 6/1985 | Baranyi et al. | 564/307 |
| 4,524,220 | 6/1985 | Law | 564/307 |
| 4,552,822 | 11/1985 | Kazmaier et al. | 564/307 X |
| 4,559,286 | 12/1985 | Kazmaier et al. | 430/59 |

Primary Examiner—Robert V. Hines
Attorney, Agent, or Firm—E. O. Palazzo

[57] ABSTRACT

A process for the preparation of squaraine compounds which comprises reacting an aromatic amine or mixtures of such amines with squaric acid or squaric acid derivatives in the presence of an aliphatic alcohol and a trialkylorthoformate.

27 Claims, No Drawings

PROCESSES FOR SQUARAINE COMPOUNDS

BACKGROUND OF THE INVENTION

This invention is generally directed to processes for preparing squaraine compounds; and more specifically the present invention is directed to processes that enable obtaining squaraine compounds of the same composition. In one embodiment of the present invention there are provided processes for the preparation of squaraine compounds wherein undesirable water is removed from the reaction by the addition of drying components such as trialkylorthoformates permitting processes that are readily scalable, and which in some instances enable products in high yields. Also, with the processes of the present invention short reaction times are possible, and complex vacuum distillation steps as utilized in the prior art are avoided. The squaraine compositions prepared in accordance with the process of the present invention are useful for incorporation into layered photoresponsive imaging devices, which are sensitive to light in the wavelength region of from about 400 to about 1,000 nanometers. Therefore, the resulting devices are responsive to visible light, and infrared illumination originating from laser printing apparatuses wherein, for example, gallium arsenide diode lasers are selected. Therefore, the specific photoresponsive devices envisioned can, for example, contain situated between a photogenerating laye, and a hole transporting layer, or situated between a photogenerating layer and a supporting substrate, a photoconductive composition comprised of the squaraines prepared in accordance with the process of the present invention.

Numerous different xerographic photoconductive members with squaraines, and processes for the preparation thereof are known. Thus, for example, there is illustrated in U.S. Pat. No. 4,415,639, the disclosure of which is totally incorporated herein by reference, the use of known squaraine compositions, such as hydroxy squaraines, as a photoconductive layer in an infrared sensitive photoresponsive device. More specifically, there is described in this patent an improved photoresponsive device containing a substrate, a hole blocking layer, an optional adhesive interfacial layer, an inorganic photogenerating layer, a photoconductive composition capable of enhancing or reducing the intrinsic properties of the photogenerating layer, which photoconductive composition is selected from various squaraine compositions, including hydroxy squaraine compositions, and a hole transport layer.

Other U.S. Pat. Nos. disclosing photoconductive devices with squaraines are 4,471,041; 4,486,520; 4,508,803; 4,507,480; 4,624,904; 4,524,218; 4,524,220; 4,521,621; 4,523,035; 4,390,610; 4,353,971; 4,391,880; 4,524,219; 4,525,592; 4,559,286; 4,585,895; 4,585,884; 4,607,124; 4,606,986; 4,621,038; 4,628,018; 4,552,822; 3,617,270; 3,824,099; 4,150,987; 4,175,956; 4,353,971; 4,390,610; 4,391,888; 4,500,621; 4,123,270; and 4,481,270. Although processes for the preparation of squaraines are illustrated in the aforementioned patents, there are no teachings therein where water is removed by the utilization of drying components, rather these prior art processes employ, for example, the use of azeotropic agents and distillation steps; and wherein the yield of scale up product is substantially lower in some instances than the yields obtained with certain process embodiments of the present invention.

More specifically, processes for preparing squaraine compositions are well known and generally involve the reaction of squaric acid, an alkyl ester of squaric acid, a dialkyl ester of squaric acid, or an aryl substituted squaric acid derivative with an aromatic amine. Thus, for example, squaraine compounds can be prepared by the reaction at a temperature of from about 50° C. to about 130° C. of an aromatic amine and squaric acid in a molar ratio of from about 1.5:1 to 4:1 in the presence of a mixture of an aliphatic alcohol and an optional azeotropic cosolvent. About 200 milliliters of alcohol per 0.1 mole of squaric acid are used, while from about 40 milliliters to about 4,000 milliliters of azeotropic material are selected. Illustrative examples of amine reactants include N,N-dialkylanilines, while examples of aliphatic alcohols selected are primary alcohols, especially 1-butanol and 1-heptanol. Azeotropic materials include aliphatic and aromatic compositions inclusive of benzene and toluene. Also, it is known that the stoichiometry of the reaction of squaric acid with aromatic amines produces 2 mole equivalents of water, while the reaction of an alkyl squarate with aromatic amines produces one mole equivalent of water; and the reaction of 3-(4'-N,N-dimethylaminophenyl)-4-hydroxycyclobutene-1,2-dione with aromatic amines generates one mole equivalent of water.

Moreover, it is known that water present in the reaction mixture should be removed quickly and completely. In some situations, as little as 0.05 percent of water in the reaction mixture can lower the yield appreciably. Thus, there is disclosed in U.S. Pat. No. 4,500,621 a process for obtaining squaraine compounds by the reaction of squaric acid with N,N-dimethyl-m-toluidine in 1-pentanol solvent, without water removal, and wherein the yield decreased from 56 percent at 0.05 mole scale to 43 percent at 0.5 mole scale. Water removal methods employed in the prior art include: (1) a Dean Stark trap for azeotropic distillation; (2) distillation to a Soxhlet containing molecular sieves or other drying agent, and the return of dried solvent to the reaction mixture; (3) a gentle nitrogen purge of a refluxing reaction; and (4) combinations thereof incorporating fractionation and/or vacuum distillation.

Also, there is disclosed in U.S. Pat. No. 4,523,035 a process for obtaining squaraine compounds by the reaction of squaric acid with various aromatic amines in the presence of a 1-heptanol solvent at reduced pressure with water removal by a Dean Stark trap. When this process is applied to bis(4-(N-methyl-N-(p-chlorobenzyl)amino)phenyl)squaraine, the reaction yield decreases from 75 percent at a 2 liter to 52 percent at a 20 liter scale. While it is not intended to be limited by theory, extrapolation of these medium scale results indicates larger scale forecast yields of about 20 percent at a 1,000 liter scale of reaction. In addition, when preparing squaraine compounds wherein toluene and 1-butanol mixed solvent systems are selected, and there are utilized molecular sieves, there results a decrease of yield upon scale up of, for example, from about 56 percent at 200 milliliters scale to 40 percent at a 1 liter scale. Similarly, the selection of a toluene and 1-octanol mixed solvent with molecular sieves and a Soxhlet apparatus at atmospheric pressure provide squaraines with a yield decrease of from 42 percent at 200 milliliters scale to 18 percent at a 5 liter scale. In contrast, with certain embodiments of the present invention, reference for example working Examples IV and V, there results squaraines of high yields which are independent of scale, that is the yield is 80 percent at 200 milliliters scale and 82 percent at a 20 liter scale.

Additionally, there is disclosed in U.S. Pat. No. 4,524,219, the disclosure of which is totally incorporated herein by reference, a process for the preparation of squaraine compositions which comprises reacting an alkyl squarate with an aniline in the presence of an optional acid catalyst. Water formed during the reaction was removed by a Dean Stark trap or nitrogen gas flow. While it is not intended to be limited by theory, it is believed that substantially the same or similar intermediates, namely squaric acid, alkyl squarate, and dialkyl squarate, are involved in this process as in similar processes starting from squaric acid with the result that water removal is necessary to obtain good yields.

Furthermore, there is disclosed in U.S. Pat. No. 4,525,592, the disclosure of which is totally incorporated herein by reference, a squaraine process wherein there is reacted a dialkyl squarate and a N,N-dialkylaniline in the presence of an acid catalyst, at a temperature of from about 60° C. to about 160° C., and in the presence of water saturated aliphatic alcohol solvents, such as methanol, ethanol, propanol, butanol and the like. Furthermore, it is known that this process requires the initial presence of water in a water saturated alcohol solvent, although this and subsequent water formed during the reaction is removed by a nitrogen gas flow.

Moreover, there is also disclosed in U.S. Pat. No. 4,524,220, the disclosure of which is totally incorporated herein by reference, a process for the preparation of squaraine compositions which comprises the reaction of squaric acid with an aromatic aniline in the presence of an aliphatic amine, and wherein a Dean Stark trap was employed for water removal.

Also, there are illustrated in U.S. Pat. Nos. 4,559,286 and 4,607,124, the disclosures of which are totally incorporated herein by reference, processes for obtaining mixed squaraine compositions by the reaction of squaric acid with two aromatic anilines, specifically 3-fluoro-N,N-dimethylaniline and 3-methyl-N,N-dimethylaniline in the presence of 1-heptanol solvent, wherein water is removed, for example, by the combined influence of a partial vacuum reflux to a Dean Stark trap at 40 Torr, reference Table 1. More specifically, with the process of the U.S. Pat. No. '286 the yield decreases, for example, from 45 percent to 25 percent upon an 80 fold scale-up to 8 mole scale. Also, the composition of the squaraine product varies substantially as a consequence of the difference in reactivity of the two amines. In particular, the fluorine content of the squaraine composition decreases from 1.46 to 0.76 percent. In contrast, with the process of the present invention as illustrated in Example IX there results a 50 percent yield of product, which product composition was independent of scale.

Additionally, there is disclosed in U.S. Pat. No. 4,606,986 a process for obtaining mixed squaraine compositions by the reaction of squaric acid with N,N-dimethylaniline and 3-methyl-N,N-dimethylaniline wherein the yield decreases, for example, from 82 percent with a 500 milliliter reaction to 70 percent with a 12 liter reaction.

Furthermore, there is disclosed in U.S. Pat. No. 4,585,895, the disclosure of which is totally incorporated herein by reference, a process for the preparation of mixed squaraine compositions which comprises reacting a dialkyl squarate, a dialkylaniline and a dialkylhaloaniline in the presence of an aliphatic alcohol and an optional acid catalyst. In this process, there is selected water in a water saturated alcohol solvent, which water is subsequently removed.

Additionally there is disclosed in U.S. Pat. No. 4,624,904 a process for obtaining unsymmetrical squaraines by, for example, the reaction of 3-(4'-N,N-dimethylaminophenyl)-4-hydroxycyclobutene-1,2-dione with various ring substituted N,N-dimethylanilines in 1-heptanol solvent at 40 Torr with a Dean Stark trap.

Although the above processes for preparing squaraine compositions are suitable for their intended purposes, there continues to be a need for other processes wherein photoconductive squaraine compositions can be prepared. Additionally, and more specifically there remains a need for simple, economical processes for preparing squaraine compositions with stable properties, which squaraines can be incorporated into photoconductive devices. Moreover, there remains a need for processes that enable in some instances the preparation of squaraine products in high yields. In addition, there remains a need for processes that will enable the preparation of squaraine photogenerating pigments wherein complex distillation steps, and especially vacuum processes, are avoided for water removal. There is also a need for the preparation of squaraine compounds wherein the formed water subsequent to treatment can remain in the reaction mixture. Additionally, there is a need for commercial processes for the preparation of squaraine compounds in yields of greater than 80 percent. Also, there is a need for large scale commercial processes with short reaction times, with high throughput (grams of squaraine per liter of reactor), and wherein inexpensive alcohol solvents and cosolvents can be selected. Further, there is a need for processes wherein there is selected low mole ratios of amine to squaric acid reactants, which processes enable lower energy requirements as refluxing conditions are avoided. Moreover, there is a need for processes wherein symmetrical squaraines, mixed squaraines, unsymmetrical squaraines, and other similar squaraines as illustrated in the appropriate aforementioned patents are prepared, and wherein water is removed therefrom by the addition of a trialkylorthoformate. There is also a need for processes enabling the preparation of squaraine compounds wherein the rate of the chemical generation of water is substantially equivalent to the rate at which the water is chemically removed by the addition of a trialkylorthoformate. With respect to the aforementioned process, the water removing trialkylorthoformate does not react adversely with the starting reaction component such as a squaric acid or aromatic amine; can be readily separated from the resulting product; reacts preferentially with water in the presence of excess amounts of alcohol; is inexpensive and readily available; and does not adversely effect the xerographic properties of the squaraine product generated.

SUMMARY OF THE INVENTION

It is therefore an object of the present invention to provide processes for preparing squaraine compounds.

In another object of the present invention there are provided improved processes for preparing squaraine compositions in acceptable yields with consistent compositions independent of reaction scale.

In yet another object of the present invention there are provided simple, economical processes for preparing squaraine compounds wherein water removal is accomplished in a simple, and economical manner, which water or reaction products therefrom can be retained in the reaction mixture subsequent to the treatment thereof.

A further object of the present invention resides in improved processes for obtaining squaraine compositions of excellent sensitivity, and acceptable cyclability when incorporated into layered imaging members with hole transport molecules.

In yet another object of the present invention there are provided simple low energy processes where refluxing is not required.

Another object of the present invention resides in the provision of a simple inexpensive process wherein lower aliphatic alcohols and inexpensive cosolvents are employed.

Also in yet another object of the present invention there are provided simple one step syntheses of symmetrical or mixed squaraines from squaric acid.

Further in yet another object of the present invention there are provided simple processes with rapid reaction times of, for example, 15 minutes.

In yet another object of the present invention there are provided simple processes with high throughput (grams yield of product per liter of reactor).

A further object of the present invention is to provide processes for chemical water removal to compete with chemical water generation such that: (1) acceptable yields of squaraine compounds are obtained; (2) the trialkylorthoformate selected can be readily separated from the product at the end of the reaction; (3) the trialkylorthoformate reacts preferentially with water in the presence of alcohol; and (4) there results squaraine compositions with excellent xerographic sensitivity, acceptable dark decay values, and superior cycling properties.

These and other objects of the present invention are accomplished by simple economical processes for the preparation of squaraine compounds. More specifically, the process of the present invention relates to the preparation of squaraine compounds, which comprises the reaction of an aromatic amine with squaric acid, and/or squarate esters in the presence of an alcohol, and a trialkylorthoformate. This is enabled as a result of the reaction of the formate with water the formation of an alkyl formate, and an alcohol. The resulting squaraine compounds, subsequent to separation from the reaction mixture, can be selected as photogenerating pigments for incorporation into layered photoconductive imaging members.

In one embodiment of the present invention, there is provided a process for accomplishing the preparation of symmetrical squaraine compounds selected from the group consisting of unsubstituted squaraines, hydroxy squaraines, fluorinated squaraines, benzyl squaraines, and mixtures thereof, as illustrated in the patents recited hereinbefore, the disclosures of each being totally incorporated herein by reference, by reacting, for example, from about 1 mole equivalent to about 6 mole equivalents, and preferably from about 1 mole equivalent to about 4 mole equivalents of an aromatic amine with squaric acid in a solvent comprising from about 0.5 liter per mole to about 50 liters per mole, and preferably from about 0.5 liter per mole to about 10 liters per mole of an aliphatic alcohol containing from about 50 grams per mole to about 1,500 grams per mole, and preferably from about 300 grams per mole to about 1,000 grams per mole of a trialkylorthoformate; an optional cosolvent in an amount of from about 0.02 to about 100 liters per mole; an optional acid catalyst in an amount of from about 0.01 mole equivalents to about 50 mole equivalents; and an optional aliphatic amine in an amount of from about one milliliter to about 50 milliliters per mole; thereafter heating the reaction mixture at a temperature of from about 40° C. to about 160° C., and preferably from about 70° C. to about 120° C., for a reaction time of from about 15 minutes to about 50 hours; separating the formed squaraine product therefrom, and wherein water formed during the reaction is converted into alkyl formate and an alcohol.

In another embodiment of the present invention, there is provided a process for accomplishing the preparation of mixed squaraine compounds selected from mixtures of unsubstituted squaraines, alkyl squaraines, hydroxyl squaraines, fluorinated squaraines, and benzyl squaraines as illustrated in the patents recited hereinbefore, the disclosures of each being totally incorporated herein by reference, by reacting, for example, from about 1 mole equivalent to about 6 mole equivalents, and preferably from about 1 mole equivalent to about 4 mole equivalents of a mixture of two or more different aromatic amines with squaric acid in a solvent comprising from about 0.5 liter per mole to about 50 liters per mole, and preferably from about 0.5 liter per mole to about 10 liters per mole of an aliphatic alcohol containing from about 50 grams per mole to about 1,500 grams per mole, and preferably from about 300 grams per mole to about 1,000 grams per mole of a trialkylorthoformate; an optional amount, from about 0.02 to about 100 liters per mole, of a cosolvent; and an optional amount, from about 0.01 to about 50 mole equivalents, of an acid catalyst; and an optional amount, from about 1 to about 50 milliliters per mole of an aliphatic amine, thereafter heating the reaction mixture at a temperature of from about 40° C. to about 160° C., and preferably from about 70° C. to about 120° C., for a reaction time of from about 15 minutes to about 50 hours; separating the formed squaraine product therefrom; and wherein water formed during the reaction is converted into alkyl formate and an alcohol.

Another embodiment of the present invention resides in a process for accomplishing the preparation of unsymmetrical squaraine compounds selected from the group consisting of alkyl squaraines, hydroxy squaraines, fluorinated squaraines, and benzyl squaraines, as illustrated in the patents recited hereinbefore, the disclosures of each being totally incorporated herein by reference, by reacting, for example, from about 0.5 mole equivalent to about 50 mole equivalents, and preferably from about 1 mole equivalent to about 5 mole equivalents of an aromatic amine with an aryl substituted squaric acid derivative in a solvent comprising from about 1 liter per mole to about 100 liters per mole, and preferably from about 2 liters per mole to about 20 liters per mole of an aliphatic alcohol containing from about 50 grams per mole to about 1,500 grams per mole, and preferably from about 300 grams per mole to about 1,000 grams per mole of a trialkylorthoformate; an optional amount, from about 0.02 to about 100 liters per mole of a cosolvent; an optional amount, from about 0.01 to about 50 mole equivalents of an acid catalyst; and an optional amount, from about 1 to about 50 milliliters per mole of an aliphatic amine; thereafter heating the reaction mixture at a temperature of from about 40° C. to about 160° C., and preferably from about 70° C. to about 120° C., for a reaction time of from about 15 minutes to about 50 hours; separating the formed squaraine product therefrom; and wherein water formed during the reaction is converted into alkyl formate and an alcohol.

Illustrative examples of squaraine compounds that can be prepared with the process of the present invention include those as indicated herein and detailed in the U.S. patents mentioned, the disclosures of which are totally incorporated herein by reference, including hydroxy squaraines, unsubstituted squaraines, fluoro squaraines, benzylfluorinated squaraines, chlorobenzyl squaraines, squaraine mixtures containing, for example, bis(4-dimethylaminophenyl)squaraine, (2-fluoro-4-dimethylamino)(4-dimethylaminophenyl)squaraine, and bis(2-fluoro-4-dimethylaminophenyl)squaraine; the squaraines as illustrated in U.S. Pat. No. 4,426,434, the disclosure of which is totally incorporated herein by reference; and the like. Preferred squaraine compounds prepared in accordance with the process of the present invention in yields of from about 35 to about 95 percent in some instances include bis(4-dimethylaminophenyl) squaraine, bis(2-fluoro-4-dimethylaminophenyl) squaraine, bis(2-methyl-4-dimethylaminophenyl) squaraine, bis(4-(N-methyl-N-benzylamino)-2-fluorophenyl) squaraine, bis(4-(N-methyl-N-benzylamino)phenyl) squaraine, bis(4-(N-methyl-N-(p-chlorobenzyl)amino)-2-fluorophenyl) squaraine, chlorobenzyl squaraine, (2-fluoro-4-dimethylaminophenyl) (4-dimethylaminophenyl) squaraine, (2-hydroxy-4-dimethylaminophenyl) (4-dimethylaminophenyl) squaraine, (2-fluoro-4-dimethylaminophenyl) (4-(N-methyl-N-(p-chlorobenzyl)amino)phenyl)squaraine; mixtures of squaraines, inclusive of mixtures of bis(4-dimethylaminophenyl) squaraine, bis(2-fluoro-4-dimethylaminophenyl) squaraine, and (2-fluoro-4-dimethylaminophenyl) (4-dimethylaminophenyl)squaraine; and the like.

Examples of aromatic amines, utilized in amounts of from about 0.5 to 50 mole equivalents include indoles, pyrroles, naphthalene amine compounds, 8-hydroxyjulolidine, 8,10-dihydroxyjulolidine, N,N-dimethylaniline, 3-dimethylaminophenol, 3-fluoro-N,N-dimethylaniline, 3-methyl-N,N-dimethylaniline, N,N-dialkylanilines, N-methyl-N-(p-chlorobenzyl)aniline, 3-fluoro-N-methyl-N-(p-chlorobenzyl)aniline, .N,N-dibenzylanilines, ring substituted N,N-dibenzylanilines, N-alkyl-N-benzylanilines, ring substituted N-alkyl-N-benzylanilines, 3,5-dimethyl-N,N-dimethylaniline, 3-dimethylamino-5-methylphenol; and the like.

Examples of squaric acids and squarate esters utilized in amounts of from about 0.01 to 1,000 moles include squaric acid, monoalkyl esters of squaric acid, dialkyl esters of squaric acid, 3-(4'-N,N-dimethylaminophenyl)-4-hydroxycyclobutene-1,2-dione, aromatic ring substituted 3-(4'-N,N-dimethylaminoaryl)-4-hydroxycyclobutene-1,2-diones, 3-(4'-N,N-dimethylaminophenyl)-4-alkoxycyclobutene-1,2-diones, aromatic ring substituted 3-(4'-N,N-dimethylaminoaryl)-4-alkoxycyclobutene-1,2-diones, 3-(4'-N,N-dimethylaminophenyl)-4-chlorocyclobutene-1,2-dione, and aromatic ring substituted 3-(4'-N,N-dimethylaminoaryl)-4-chlorocyclobutene-1,2-diones, with squaric acid, and 3-(4'-N,N-dimethylaminoaryl)-4-hydroxycyclobutene-1,2-diones being preferred.

As illustrative examples of aliphatic alcohols selected in amounts of from about 0.5 to 100 liters per mole of squaric acid or squaric acid derivative, there are selected those containing from about 1 carbon atom to about 20 carbon atoms, and preferably from about 2 carbon atoms to about 8 carbon atoms, including mixtures of these alcohols. Specific examples of aliphatic alcohols selected for the process of the present invention include ethanol, propanol, 1-butanol, 1-pentanol, hexanol, octanol, 2-ethylhexanol, benzyl alcohols, glycols, ether alcohols such as methoxyethanol, ethoxyethanol, glyme alcohols, and the like; and halogenated alcohols such as 2-chloroethanol, and the like; with octanol, hexanol, 1-pentanol, 1-butanol, propanol, ethanol, 2-ethylhexanol and 2-chloroethanol being preferred.

As trialkylorthoformates present in an amount of, for example, from about 50 to about 1,500 grams per mole of squaric acid reagent, there can be selected for the process of the present invention trimethylorthoformate, triethylorthoformate, tripropylorthoformate, tributylorthoformate, and the like.

As examples of optional cosolvents selected in amounts from about 0.02 to about 100 liters per mole of squaric acid reagent, there can be selected one or more of an aliphatic or an aromatic hydrocarbon with from 1 to about 15 carbon atoms, haloaromatic compounds, halogenated aliphatics, ethers; and other nonreactive solvents, including cyclohexane, hexane, heptane, decane, octane, toluene, xylene, methylene chloride, dichloroethene, chlorobenzene, and the like.

Examples of optional catalysts selected in amounts of from about 0.01 to about 50 mole equivalents per mole of squaric acid reagent, include sulfuric acid, acetic acid, oxalic acid, 2,2,2-trifluoroacetic acid, trichloroacetic acid, toluene sulfonic acid, and the like; with acetic acid, trichloroacetic acid and sulfuric acid being preferred. These acids can be employed to vary the total alcohol concentration to adjust the solvent polarity to a value which provides higher product yields to enable squaraine compositions with improved dark decay.

Examples of optional aliphatic amines selected in amount from about 1 to 50 milliliters per mole of squaric acid derivative include those containing from about 4 carbon atoms to about 20 carbon atoms, such as butylamine, hexylamine, octylamine, and the like; with octylamine being preferred.

The reaction of the present invention is accomplished at any suitable temperature that will enable the desired products to form. Generally, the reaction is accomplished at a temperature of from about 40° C. to about 160° C., and preferably from about 70° C. to about 120° C. Also, the reaction is conducted for a time that will enable the desired products to form, thus generally, the reaction is accomplished in a time of from about 15 minutes to about 50 hours; with from about 1 hour to about 16 hours being preferred.

Also, the reaction time and proportion of reactants, primary alcohol, trialkylorthoformate, and optional components selected depend on a number of factors including, for example, the specific reactants used, the reaction temperature, the alcohol selected, interrelationships among these variables, and the like. Optimum reaction conditions reflect a balance among competing forces and competing requirements; increased reaction rate with increased alcohol concentration; increased side reactions with increased alcohol concentration; increased drying ability with increased trialkylorthoformate concentration; increased throughput with increased squaric acid concentration; and increased catalysis with increased acid concentration.

The reaction products were identified primarily by melting point data, visible absorption spectroscopy, nuclear magnetic resonance spectroscopy, mass spectroscopy, and elemental analyses for the respective substituents, such as analyses for carbon, hydrogen, nitrogen, and chlorine or fluorine, if appropriate. The data generated from analysis was compared with the data available for identical compounds prepared from prior art squaraine processes.

Further, the squaraine compounds obtained in accordance with the process of the present invention can be incorporated into photoconductive imaging members. One such member is comprised of a supporting substrate, a hole transport layer; and as a photoconductive layer situated between the supporting substrate and the hole transport layer, the squaraine compositions prepared in accordance with the process of the present invention. In another embodiment, there is envisioned a layered photoresponsive device comprised of a supporting substrate, a photoconductive layer comprised of a squaraine compound formulated with the process of the present invention, and situated between the supporting substrate and the photoconductive layer a hole transport layer. Also, provided in accordance with the present invention are improved photoresponsive devices useful in printing systems comprising a layer of a photoconductive composition situated between a photogenerating layer and a hole transport layer; or wherein the photoconductive composition is situated between a photogenerating layer and the supporting substrate of such a device, the photoconductive composition being comprised of the squaraines obtained with the process of the present invention. In the latter devices, the photoconductive layer serves to enhance, or reduce the intrinsic properties of the photogenerating layer in the infrared and/or visible range of the spectrum.

In one specific illustrative embodiment, the photoresponsive device can be comprised in the order stated of (1) a supporting substrate, (2) a hole blocking layer, (3) an optional adhesive interface layer, (4) a photoconducting composition layer capable of enhancing or reducing the intrinsic properties of the photogenerating layer, which composition is comprised of the squaraine compounds formulated in accordance with the process of the present invention, and (5) a hole transport layer. Thus, a specific photoresponsive device can be comprised of a conductive supporting substrate, a hole blocking metal oxide layer in contact therewith, an adhesive layer, a photoconducting composition capable of enhancing or reducing the intrinsic properties of the photogenerating layer in the infrared and/or visible range of the spectrum, which composition is comprised of the squaraine compounds obtained in accordance with the process of the present invention; and as a top layer, a hole transport layer comprised of certain diamines dispersed in a resinous matrix. The photoconductive layer composition when in contact with the hole transport layer is capable of allowing holes generated by the photogenerating layer to be transported. Further, the photoconductive layer does not substantially trap holes generated in the photogenerating layer, and also the photoconductive squaraine composition layer can function as a selective filter allowing light of a certain wavelength to penetrate the photogenerating layer.

In another specific illustrative embodiment, the photoresponsive device can be comprised in the order stated of (1) a supporting substrate, (2) a hole blocking layer, (3) an optional adhesive interface layer, (4) a hole transport layer, and (5) a photoconducting composition layer capable of enhancing or reducing the intrinsic properties of the photogenerating layer, which composition is comprised of the squaraine compounds formulated in accordance with the process of the present invention.

The photoresponsive devices described herein can be incorporated into various imaging systems, such as those conventionally known as xerographic imaging processes. Additionally, those photoresponsive devices containing an inorganic photogenerating layer, and a photoconductive layer comprised of the squaraines can function simultaneously in imaging and printing systems with visible light and/or infrared light. In this embodiment, the photoresponsive devices may be negatively charged, exposed to light in a wavelength of from about 400 to about 1,000 nanometers, either sequentially or simultaneously, followed by developing the resulting image and transferring to paper. The above sequence may be repeated many times. Examples of aryl amine hole transport molecules that may be selected for the photoconductor devices are illustrated in U.S. Pat. No. 4,265,990, the disclosure of which is totally incorporated herein by reference.

The following examples are being supplied to further define various species of the present invention, it being noted that these examples are intended to illustrate and not limit the scope of the present invention. Parts and percentages are by weight unless otherwise indicated.

EXAMPLES I to III

There were prepared three mixed squaraine composition products in accordance with the process described in Example XII of U.S. Pat. No. 4,607,124, the disclosure of which is totally incorporated herein by reference, by varying the scale of the reaction by increasing the number of moles of squaric acid, the number of moles of the amines 3-fluoro-N,N-dimethylaniline and 3-methyl-N,N-dimethylaniline in proportion to the number of moles of squaric acid, and by increasing the amount of 1-heptanol solvent employed. The yields and fluorine contents of these mixed squaraine compositions are as follows:

| Comparative Example | Moles of Squaric Acid | Liters of 1-Heptanol | Percent Yield | Percent F* in Product |
|---|---|---|---|---|
| I | 0.1 | 0.4 | 45 | 1.46 |
| II | 0.4 | 0.6 | 39 | 1.09 |
| III | 8.0 | 11.9 | 25 | 0.76 |

*Percentage of flourine as determined by combustion anlysis.

These results indicate that scale-up of this reaction leads to a decrease in the yield of product. Additionally, scale-up also causes a change in the composition of the mixed squaraine product as reflected in the decreasing percent F in the product. Therefore, the compositions of products from scaled-up Examples II and III differ from the composition of the product from Example I which contains 74,67 percent bis(2-methyl-4-dimethylaminophenyl) squaraine, 22.71 percent (2-fluoro-4-dimethylaminophenyl) (2-methyl-4-dimethylaminophenyl) squaraine, and 2.62 percent bis(2-fluoro-4-dimethylaminophenyl) squaraine. The composition of the squaraine product from Example III was 83.7 percent bis(2-methyl-4-dimethylaminophenyl)squaraine, 15.6 percent (2-fluoro-4-dimethylaminophenyl) (2-methyl-4-dimethylaminophenyl) squaraine, and 0.7 percent bis(2-fluoro-4-dimethylaminophenyl) squaraine.

EXAMPLE IV

Small Scale Synthesis of Chlorobenzyl Squaraine

There was prepared the chlorobenzyl squaraine bis(4-(N-methyl-N-(p-chlorobenzyl)amino)phenyl) squaraine by reacting 3.00 grams, 26.3 millimoles, of squaric acid with 18.53 grams, 80.0 millimoles, of N-methyl-N-(p-chlorobenzyl)aniline in a solvent comprised of 29.2 milliliters of n-butanol and 44.8 milliliters of toluene, to which was added 19.3 grams, 130 millimoles, of triethylorthoformate. This reaction mixture was refluxed for 5 hours. Thereafter, the reaction mixture was permitted to cool to room temperature. Subsequently, there was separated by filtration 11.41 grams, 21.1 millimoles, in 80.0 percent yield, a blue-green crystalline product of the above chlorobenzyl squaraine.

EXAMPLE V

Medium Scale Synthesis of Chlorobenzyl Squaraine

There was prepared the chlorobenzyl squaraine bis(4-(N-methyl-N-(p-chlorobenzyl)amino)phenyl) squaraine by reacting 370.5 grams, 3.25 moles, of squaric acid with 2.26 kilograms, 9.77 moles, of N-methyl-N-(p-chlorobenzyl) aniline in a solvent comprised of 4.34 liters of n-butanol and 6.67 liters of toluene, to which was added 2.39 kilograms of triethylorthoformate. This reaction mixture was refluxed for 6 hours. Thereafter, the reaction mixture was cooled to room temperature. Subsequently, there was separated by filtration 1.45 kilograms, 2.68 moles, in 82.3 percent yield, the above squaraine.

EXAMPLE VI

Synthesis of Chlorobenzyl Squaraine using 2-Chloroethanol:

There was prepared the chlorobenzyl squaraine bis(4-(N-methyl-N-(p-chlorobenzyl)amino)phenyl) squaraine by reacting 3.01 grams, 26.4 millimoles, of squaric acid with 18.45 grams, 79.7 millimoles, of N-methyl-N-(p-chlorbenzyl)aniline in a solvent comprised of 40 milliliters of 2-chloroethanol and 16.3 milliliters of toluene, to which was added 32.1 grams, 217 millimoles, of triethylorthoformate. This reaction mixture was refluxed for 1 hour. Thereafter, the reaction mixture was permitted to cool to room temperature. Subsequently, there was separated by filtration 4.78 grams, 8.83 millimoles, 33.4 percent yield, the above squaraine.

EXAMPLE VII

Synthesis of Unsubstituted Squaraine (Aniline in Excess):

There was prepared bis(4-dimethylaminophenyl) squaraine by reacting 2.01 grams, 17.6 millimoles, of squaric acid with 5.74 grams, 4.72 millimoles, of N,N-dimethylaniline in a solvent comprised of 20 milliliters of ethanol, and 20 milliliters of toluene, to which was added 40 milliliters of triethylorthoformate, and 20 milliliters of acetic acid. This reaction mixture was refluxed for 5 hours. Thereafter, the reaction mixture was permitted to cool to room temperature. Subsequently, there was separated by filtration 1.85 grams, 5.76 millimoles, 32.7 percent yield, a blue crystalline product of the above squaraine.

EXAMPLE VIII

Synthesis of Unsubstituted Squaraine (Squaric Acid in Excess):

There was prepared bis(4-dimethylaminophenyl) squaraine by reacting 5.01 grams, 43.9 millimoles, of squaric acid with 5.74 grams, 47.2 millimoles, of N,N-dimethylaniline in a solvent comprised of 20 milliliters of ethanol, and 20 milliliters of toluene, to which was added 40 milliliters, of triethylorthoformate, and 20 milliliters of acetic acid. This reaction mixture was refluxed for 5 hours. Thereafter, the reaction mixture was permitted to cool to room temperature. Subsequently, there was separated by filtration 4.66 grams, 14.5 millimoles, 61.6 percent yield, the above squaraine.

EXAMPLE IX

Mixed F/Methyl Squaraines

There was prepared a mixed squaraine composition containing bis(2-fluoro-4-dimethylaminophenyl) squaraine, bis(2-methyl-4-dimethylaminophenyl) squaraine, and (2-fluoro-4-dimethylaminophenyl) (2-methyl-4-dimethylaminophenyl) squaraine by reacting 5.0 grams, 44 millimoles, of squaric acid with 5.41 grams, 39 millimoles, of 3-fluoro-N,N-dimethylaniline, and 6.49 grams, 48 millimoles, of 3-methyl-N,N-dimethylaniline in a solvent comprised of 36.4 milliliters of n-butanol and 34.3 milliliters of toluene, to which was added 36.2 grams of triethylorthoformate. This reaction mixture was refluxed for 6.3 hours. Thereafter, the reaction mixture was permitted to cool to room temperature. Subsequently, there was separated by filtration 5.54 grams, 50.2 percent yield, a greenish gold cubic crystalline product of the above mixed squaraine composition as identified by NMR spectroscopy, 7 percent bis(2-fluoro-4-dimethylaminophenyl) squaraine; 28 percent (2-fluoro-4-dimethylaminophenyl) (2-methyl-4-dimenthylaminophenyl) squaraine; and 65 percent bis(2-methyl-4-dimethylaminophenyl) squaraine.

|  | C | H | N | F |
|---|---|---|---|---|
| Calculated | 74.05 | 6.55 | 8.00 | 2.26 |
| Found | 74.37 | 6.55 | 8.04 | 2.20 |

EXAMPLE X

Unsymmetrical H/F Squaraine

There was prepared an unsymmetrical squaraine (2-fluoro-4-dimethylaminophenyl) (4-dimethylaminophenyl) squaraine by reacting 1.00 gram, 4.60 millimoles, of 3-(4'-N,N-dimethylaminophenyl)-4-hydroxycyclobutene-1,2-dione with 1.29 grams, 9.29 millimoles, of 3-fluoro-N,N-dimethylaniline in 12.7 milliliters of n-butanol, to which was added 5.60 grams of triethylorthoformate, and 2.52 grams of acetic acid. This reaction mixture was refluxed for 5 hours. Thereafter, the reaction mixture was permitted to cool to room temperature. Subsequently, there was separated by filtration 739 milligram, 2.18 millimoles, 47.5 percent yield, a blue crystalline product of the above unsymmetrical squaraine with a Lambda max 630 nanometer in methylene chloride.

EXAMPLE XI

Unsymmetrical H/OH Squaraine

There was prepared the unsymmetrical squaraine (2hydroxy-4-dimethylaminophenyl) (4-dimethylaminophenyl) squaraine by reacting 6.52 grams, 30 millimoles, of 3-(4'-N,N-dimethylaminophenyl)-4-hydroxycyclobutene-1,2-dione with 4.12 grams, 30 millimoles, of 3-dimethylaminophenol in a solvent comprised of 300 milliliters of n-butanol, and 150 milliliters of toluene, to which was added 13.23 grams of triethylorthoformate. This reaction mixture was refluxed using a Dean Stark trap and gentle nitrogen purge for 5 hours. Thereafter, the reaction mixture was permitted to cool to room temperature. Subsequently, there was separated by filtration 9.72 grams, 28.9 millimoles, 96.3 percent yield, a crystalline product of the above unsymmetrical squaraine.

EXAMPLE XII

Unsymmetrical F/Chlorobenzyl Squaraine

There was prepared the unsymmetrical squaraine (2-fluoro-4-dimethylaminophenyl) (4(N-methyl-N-(p-chlorobenzyl)amino)phenyl) squaraine by reacting 7.00 grams, 29.8 millimoles, of 3-(2'-fluoro-4'-N,N-dimethylaminophenyl)-4-hydroxycyclobutene-1,2-dione with 8.63 grams, 37.2 millimoles, of N-methyl-N-(p-chlorobenzyl) aniline in a solvent comprised of 300 milliliters of n-butanol, and 150 milliliters of toluene, to which was added 13.23 grams of triethylorthoformate. This reaction mixture was refluxed with a Dean Stark trap and gentle nitrogen purge for 16 hours. Thereafter, the reaction mixture was permitted to cool to room temperature. Subsequently, there was separated by filtration 11.6 grams, 25.8 millimoles, 87 percent yield , a crystalline product of the above unsymmetrical squaraine.

EXAMPLE XIII

Preparation of Photoresponsive Devices Incorporating Chlorobenzyl Squaraine Composition Photoresponsive devices were prepared with the squaraine composition as prepared in Examples IV and V by providing an aluminized Mylar ® substrate of a thickness of 3 mils, followed by applying thereto with a multiple clearance film applicator in a wet thickness of 0.5 mils a layer of 3-aminopropyltrimethoxysilane, available from PCR Research Chemicals, Florida, in ethanol in a 1:50 volume ratio. This layer was then allowed to dry for 5 minutes at 110° C. in a forced air oven. There was then applied to the silane layer 0.5 percent by weight of an adhesive, available from E.I. DuPont as 49,000 polyester, in methylene chloride and 1,1,2-trichloroethane (4:1 volume ratio) with a multiple clearance film applicator to a wet thickness of 12.5 microns. This layer was allowed to dry for 1 minute at room temperature and 10 minutes at 100° C. in a forced air oven. The resulting layer had a dry thickness of 0.05 micron. A charge transporting layer was then prepared as follows:

A transport layer was prepared by mixing 50 percent by weight of Makrolon ®, a polycarbonate resin available from Larbensabricken Bayer A.G., with 50 percent by weight N,N-diphenyl'-bis(3-methylphenyl)-1,1'-biphenyl-4,4'-diamine, which was then added to methylene chloride, 13 percent by weight. All of these components were placed in an amber bottle and dissolved. The mixture was then coated to provide a whole transport layer with a dry thickness of 20 microns on top of the above prepared aluminized Mylar ® substrate, which had been overcoated with the silane and adhesive layers, using a multiple clearance film applicator of 10 mils wet gap thickness. The resulting device was then dried at room temperature for 5 minutes.

The above charge transport layer was then overcoated with a charge generating layer containing 30 percent by weight of the chlorobenzyl squaraine synthesized as described in Example IV. More specifically, in a separate 2 ounce amber bottle, there was added 0.17 gram of the chlorobenzyl squaraine (recrystallized from 2-chloroethanol), 0.40 gram of Vitel PE-200 ®, a polyester available from Goodyear, and 13.5 grams of methylene chloride. The above mixture was shaken by hand for 5 minutes. The resulting slurry was then coated on the above prepared aluminized Mylar ® substrate, which had been overcoated with the silane layer, adhesive layer and charge transporting layer, with a multiple clearance film applicator to a wet thickness of 1 mil. This layer was allowed to air dry for at least six hours. The resulting device was dried at 60° C. for 30 minutes in a forced air oven. The dry thickness of the squaraine layer was 1 micron.

EXAMPLE XIV

Preparation of Photoresponsive Devices Incorporating Mixed Fluoromethyl Squaraine Composition A photoresponsive device was fabricated with the squaraine composition as prepared in Example IX by providing an aluminized Mylar ® substrate of a thickness of 3 mils, followed by applying thereto with a multiple clearance film applicator in a wet thickness of 0.5 mils a layer of 3-aminopropyl trimethoxysilane in ethanol in a 1:50 volume ratio. This layer was then allowed to dry for 5 minutes at 110° C. in a forced air oven. There was then applied to the silane layer 0.5 percent by weight of an adhesive, available from E.I. DuPont as 49,000 polyester, in methylene chloride, and 1,1,2-trichloroethane (4:1 volume ratio) with a multiple clearance film applicator to a wet thickness of 12.5 microns. This layer was then allowed to dry for one minute at room temperature and 10 minutes at 100° C. in a forced air oven. The resulting layer had a dry thickness of 0.05 micron. A photoconductive layer containing 30 percent by weight of the mixed fluoromethyl squaraine synthesized as described in Example IX was then prepared as follows:

In a separate 2 ounce amber bottle, there was added 0.30 gram of the fluoromethyl mixed squarane, 0.70 gram of Vitel PE-200 ®, 70 grams of ⅛ inch stainless steel shot, and 19 grams of methylene chloride. The above mixture was placed on a ball mill for 24 hours. The resulting slurry was then coated on the above prepared aluminized Mylar ® substrate, which has been overcoated with the silane and the 49,000 layers, with a multiple clearance film applicator to a wet thickness of 1 mil. This layer was allowed to air dry for 5 minutes. The resulting device was dried at 135° C. for 20 minutes in a forced air oven. The dry thickness of the squaraine layer was 0.5 micron.

The above photoconductive layer was then overcoated with a charge transport layer, which was prepared as follows:

A transport layer composed of 65 percent by weight of Merlon 39 ®, a polycarbonate resin available from Mobay Chemical, Pennsylvania, was mixed with 35 percent by weight N,N-diphenyl'-bis(3-methylphenyl)-1,1'-biphenyl-4,4'diamine. This solution was mixed to 7 percent by weight in methylene chloride. All of these components were placed in an amber bottle and dissolved. The mixture was then coated to provide a layer with a dry thickness of 15 microns on top of the above photoconductive layer using a multiple clearance film applicator of 10 mils wet gap thickness. The resulting device was then dried at room temperature for 20 minutes and then in a forced air oven at 135° C. for 20 minutes.

EXAMPLE XV

Xerographic Evaluation of the Photoresponsive Device as Prepared in Example XIII The photoresponsive devices as prepared in Example XIII were tested for photosensitivity by charging the devices in the dark with a coroton set at +6.3 kilovolt to a surface potential of +1,050 volts, followed by measuring with an electrical probe the amount of light energy of monochromatic light of 830 nanometers supplied by a Xenon lamp, in ergs per square centimeter, required to discharge the device to one half of its surface potential. A low discharge number, for example, an $E_{\frac{1}{2}}$ of below 100, indicates excellent photosensitivity for the device involved. For the imaging device of this Example, the dark decay was about 156 volts per second, and the $E_{\frac{1}{2}}$ was about 5.3 ergs per square centimeter.

EXAMPLE XVI

Xerographic Evaluation of the Photoresponsive Device as Prepared in Example XIV

The photoresponsive devices as prepared in Example XIV were tested for photosensitivity by charging the device in the dark with a coroton set at −4.3 kilovolt to a surface potential of −830 volts, followed by measuring with an electrical probe the amount of light energy of monochromatic light of 830 nanometers supplied by a Xenon lamp, in ergs per square centimeter, required to discharge each device to one half of its surface potential. The dark decay was about 44 volts per second, and the $E_{\frac{1}{2}}$ was about 8 ergs per square centimeter.

EXAMPLE XVII

Synthesis of Chlorobenzyl Squaraine Using Trimethylorthoformate

There was prepared the chlorobenzyl squaraine bis(4-(N-methyl-N-(p-chlorobenzyl)amino)phenyl) squaraine by reacting 2.51 grams, 22.0 millimoles, of squaric acid with 15.23 grams, 65.8 millimoles, of N-methyl-N-(p-chlorobenzyl) aniline in a solvent comprised of 24.0 milliliters of n-butanol and 21.0 milliliters of toluene, to which was added 15.0 milliliters of trimethylorthoformate. This reaction mixture was shaken in a sealed bottle at 71.5° C. for 16 hours. Thereafter, the reaction mixture was permitted to cool to room temperature. Subsequently, there was separated by filtration 2.66 grams, 4.9 millimoles, 22.3 percent yeild, a blue-green crystalline product of the above squaraine.

Although the invention has been described with reference to specific embodiments, it is not intended to be limited thereto, rather those skilled in the art will recognize variations and modifications may be made therein which are within the spirit of the present invention and within the scope of the following claims.

What is claimed is:

1. A process for the preparation of squaraine compounds which comprises reacting an aromatic amine with squaric acid in the presence of an aliphatic alcohol and a trialkylorthoformate.

2. A process in accordance with claim 1 wherein there is selected a mixture of aromatic amines.

3. A process in accordance with claim 1 wherein the aromatic amine is reacted with a component selected from the group consisting of a alkyl squarate, a dialkyl squarate, and an aryl substituted squaric acid derivative.

4. A process in accordance with claim 1 wherein there is selected a mixture of at least two aromatic amines.

5. A process in accordance with claim 1 wherein there is selected as an additional reactant an aliphatic amine.

6. A process in accordance with claim 5 wherein the aliphatic amine is octyl amine.

7. A process in accordance with claim 1 wherein an acid catalyst is added thereto.

8. A process in accordance with claim 7 wherein the acid catalyst is selected from the group consisting of sulfuric acid and acetic acid.

9. A process in accordance with claim 1 wherein the squaraine compound obtained is selected from the group consisting of unsubstituted squaraines, hydroxy squaraines, and halogenated squaraines.

10. A process in accordance with claim 9 wherein the squaraine is selected from the group consisting of chlorinated squaraines and fluorinated squaraines.

11. A process in accordance with claim 1 wherein the squaraine is 2-hydroxy-4-dimethylaminophenyl-4-dimethylaminophenyl squaraine.

12. A process in accordance with claim 1 wherein the aromatic amine are selected from the group consisting of N-methyl-N-(p-chlorobenzyl) aniline, 3-fluoro-N,N-dimethylaniline and 3-methyl-N,N-dimethylaniline, N,N-dialkylanilines, julolidine, 8-hydroxyjulolidine, 8,10-dihydroxyjulolidine, 3-dimethylaminophenol, 3-fluoro-N,N-dimethylaniline, and 3-methyl-N,N-dimethylaniline.

13. A process in accordance with claim 1 wherein the trialkylorthoformate is triethylorthoformate.

14. A process in accordance with claim 1 wherein trialkylorthoformate is trimethylorthoformate.

15. A process in accordance with claim 1 wherein the aliphatic alcohol is n-butanol.

16. A process in accordance with claim 1 wherein the aliphatic alcohol contains from about 1 to about 20 carbon atoms.

17. A process in accordance with claim 1 wherein the aliphatic alcohol is selected from the group consisting of ethanol, propanol, butanol, pentanol, hexanol, octanol, 2-ethylhexanol and 2-chloroethanol.

18. A process in accordance with claim 1 wherein the reaction is accomplished at a temperature of from about 70° to about 120° C.

19. A process in accordance with claim 1 wherein there results squaraine compounds which are obtained in a yield of from about 35 to about 95 percent.

20. A process in accordance with claim 1 wherein the water formed during the reaction is converted into an alkyl formate and an alcohol.

21. A process in accordance with claim 1 wherein the squaraine compound resulting is selected as a photogenerating pigment for a layered photoconductive imaging member.

22. A process in accordance with claim 4 wherein the squaraine compound resulting is selected for incorporation into a layered photoconductive imaging member.

23. A process in accordance with claim 21 wherein the layered photocoductive imaging member is comprised of a supporting substrate, the squaraine compound and a hole transport layer.

24. A process in accordance with claim 23 wherein the hole transport layer is comprised of an aryl amine.

25. A process in accordance with claim 1 wherein the aromatic amine is employed in a mole ratio of from about 1 to about 5.

26. A process for the preparation of squaraine compounds which comprises reacting an aromatic amine with squaric acid in the presence of an aliphatic alcohol and a trialkylorthoformate, wherein at least 9.77 moles of squaric acid are employed.

27. A process in accordance with claim 26 wherein the process results in the squaraine compounds in a yield of about 82.3 percent.

* * * * *